(12) United States Patent
Kitamori et al.

(10) Patent No.: US 7,402,439 B2
(45) Date of Patent: Jul. 22, 2008

(54) METHOD OF OPERATING AN INTEGRATED STRUCTURE OF MULTILAYER FLOW MICROCHANNEL

(75) Inventors: Takehiko Kitamori, Tokyo (JP); Manabu Tokeshi, Kawasaki (JP); Akihide Hibara, Tokyo (JP)

(73) Assignee: Kanagawa Academy of Science and Technology, Kanagawa (JP)

( * ) Notice: Subject to any disclaimer, the term of this patent is extended or adjusted under 35 U.S.C. 154(b) by 490 days.

(21) Appl. No.: 10/483,233

(22) PCT Filed: Jul. 10, 2002

(86) PCT No.: PCT/JP02/00083

§ 371 (c)(1), (2), (4) Date: Jun. 15, 2004

(87) PCT Pub. No.: WO03/008981

PCT Pub. Date: Jan. 30, 2003

(65) Prior Publication Data

US 2004/0219078 A1 Nov. 4, 2004

(30) Foreign Application Priority Data

Jul. 10, 2001 (JP) ............................. 2001-209932

(51) Int. Cl.
*G01N 1/10* (2006.01)
*B01J 10/00* (2006.01)

(52) U.S. Cl. ................. 436/180; 422/129; 422/190; 422/191; 422/198; 422/200

(58) Field of Classification Search .............. 422/129, 422/190, 198, 200, 191; 436/180
See application file for complete search history.

(56) References Cited

U.S. PATENT DOCUMENTS 5,534,328 A * 7/1996 Ashmead et al. ............ 428/166

(Continued)

FOREIGN PATENT DOCUMENTS

JP 11-005029 1/1999

(Continued)

OTHER PUBLICATIONS

Manabu Tokeshi, "Zaidan Houjin Kanagawa Kagaku Gijutsu Academy, Kyoiku Kouza; Heisei 11 nendo III-ki, Bunseki System no Shuseki Course; Micro-TAS no Jissai to Tenbo", Dec. 7, 1999, Bisho Kuukan no Kagaku Kankyo Bunseki Soshi, pp. 1-5; drawings and tables, pp. 1-7; reference materials, pp. 1-23.

(Continued)

*Primary Examiner*—N. Bhat
(74) *Attorney, Agent, or Firm*—Wenderoth, Lind & Ponack, L.L.P.

(57) ABSTRACT

An integrated structure of multilayer flow microchannel, which comprises a plurality of microchannels in which parallel multilayer flow that involves the interface of fluids is formed, arranged on various positions of a substrate, wherein each of the multilayer flow microchannels is communicated with another multilayer flow microchannel. A plurality of unit operations can be carried out continuously with high efficiency on a microchip, enabling high-degree microanalysis or precise chemical synthesis using the highly integrated structure of multilayer flow microchannel.

7 Claims, 12 Drawing Sheets

U.S. PATENT DOCUMENTS

| | | | |
|---|---|---|---|
| 5,727,618 A * | 3/1998 | Mundinger et al. | 165/80.4 |
| 5,993,750 A | 11/1999 | Ghosh et al. | 422/191 |
| 6,494,614 B1 * | 12/2002 | Bennett et al. | 366/336 |
| 6,533,840 B2 * | 3/2003 | Martin et al. | 95/45 |
| 6,537,506 B1 * | 3/2003 | Schwalbe et al. | 422/130 |
| 6,572,830 B1 * | 6/2003 | Burdon et al. | 422/186.29 |
| 6,749,814 B1 * | 6/2004 | Bergh et al. | 422/130 |
| 6,759,013 B2 * | 7/2004 | Kaltenbach et al. | 422/101 |
| 6,969,506 B2 * | 11/2005 | Tonkovich et al. | 423/652 |
| 7,122,156 B2 * | 10/2006 | Bergh et al. | 422/102 |
| 7,125,540 B1 * | 10/2006 | Wegeng et al. | 423/650 |

FOREIGN PATENT DOCUMENTS

| | | |
|---|---|---|
| WO | 99/22857 | 5/1999 |

OTHER PUBLICATIONS

Akihide Hibara, Manabu Tokeshi, Keiji Uchiyama, Hideaki Hishamono, Takehiko Kitamori, Analythicak Science, 17 (1), pp. 89-93, Jan. 10, 2001.

* cited by examiner

METHOD OF OPERATING AN INTEGRATED STRUCTURE OF MULTILAYER FLOW MICROCHANNEL

TECHNICAL FIELD

The invention of the present application relates to an integrated structure of multilayer flow microchannel and a method for operating a multilayer flow by using the integrated structure of multilayer flow microchannel.

More specifically, the invention of the present application relates to a highly integrated multilayer flow microchannel structure that enables high accuracy microanalysis and precise chemical synthesis to be performed on a microchip by continuous operation with high efficiency. The invention also relates to physiochemical and chemical methods for fine operation that use the highly integrated multilayer flow microchannel structure.

BACKGROUND ART

In recent years, studies on a technique known as μ-TAS (Micro Total Analysis Systems) or Lab-on-a-Chip, in which chemical operations or physiochemical operations are integrated onto a substrate of a few square centimeters, has rapidly prevailed.

However, in such techniques, integration on a microscopic substrate, or chip, is not easy. Unlike DNA chips, wherein probes for the detection of biomolecules are immobilized, for μ-TAS or Lab-on-a-Chip, high degree integration of minute channels (microchannels) for handling liquid samples is difficult, and thus, serializing operations of complex chemical processes is not easy.

Under these conditions, the present inventors have explored the integration of complex chemical processes by combining various Unit Chemical Operations, and have previously made several proposals. In such explorations, the present inventors have made it an object to enable the handling of multilayer flow, as highly controlled fluid, within a microchannel, and to integrate such multilayer flow onto a microchip.

Hence, in consideration of the aforementioned background, an object of the present invention is to provide a highly integrated structure of multilayer flow microchannel, which enables the efficient performance of high-accuracy microanalysis, precise chemical synthesis or the like by continuous operation of a plurality of unit operations on a microchip. Further, another object of the present invention is to provide an operation method that utilizes this structure.

SUMMARY OF THE INVENTION

In order to achieve the above-described objects, a first aspect of the invention of the present application provides an integrated structure of multilayer flow microchannel, which comprises a plurality of microchannels in which parallel multilayer flow that involves the interface of fluids is formed, arranged on various positions of a substrate, wherein each of the multilayer flow microchannels is communicated with another multilayer flow microchannel.

A second aspect of the invention of the present application provides the integrated structure of multilayer flow microchannel, wherein the plurality of multilayer flow microchannels are arranged on a surface of one substrate and each multilayer flow microchannel communicates with another multilayer flow microchannel by way of a guide microchannel that identifies a specific fluid. A third aspect of the invention of the present application provides the integrated structure of multilayer flow microchannel, wherein a plurality of substrates are laminated, and the multilayer flow microchannels are arranged on surfaces of different substrates, and wherein the vertically configured multilayer flow microchannels communicate with another multilayer flow microchannel through a vertically penetrating guide hole for transporting a fluid. A forth aspect of the invention of the present application provides the integrated structure of multilayer flow microchannel, comprising a plurality of substrates that are laminated, wherein a channel for supplying a fluid to the multilayer flow microchannel and a channel for discharging a fluid from the multilayer flow microchannel are each arranged on the surface of the same or different substrate as that on which the multilayer flow microchannels are arranged.

A fifth aspect of the invention of the present application provides the integrated structure of multilayer flow microchannel, wherein a plurality of multilayer flow microchannels are configured as different unit operation regions. A sixth aspect of the invention of the present application provides the integrated structure of multilayer flow microchannel of any one of the first to fifth aspects, wherein at least one multilayer flow microchannel is configured as an analysis region.

A seventh aspect of the invention of the present application provides a method for multilayer flow operation, which comprises the use of any of the above-described integrated structures of multilayer flow microchannel. An eighth aspect of the invention of the present application provides a method for multilayer flow operation, wherein a multilayer flow involving gas/liquid fluid interface is formed within the multilayer flow microchannel. A ninth aspect of the invention of the present application provides a method for operating multilayer flow, wherein a multilayer flow involving three or more fluid layers is formed within the multilayer flow microchannel.

A tenth aspect of the invention of the present application provides a method for multilayer flow operation, which comprises the formation of a multilayer flow of three or more layers involving interfaces of fluids within microchannels arranged on a substrate. An eleventh aspect of the invention of the present application provides a method for multilayer flow operation, which comprises performing a plurality of unit operations by way of the interface of fluids in a multilayer flow of three or more layers involving interfaces of fluids.

The numbers in the drawings refer to the following:

1, 2 Multilayer flow microchannel
1A, 2A Liquid supplying channel
1B, 2B Liquid discharging channel
3 Guide microchannel
4 Multilayer flow microchannel
5 Guide hole

DETAILED DESCRIPTION OF THE INVENTION

The invention of the present application comprises the above-described characteristics. Hereinafter, further embodiments of the invention will be described.

The most important feature among the first to ninth aspects of the present invention is that a plurality of microchannels, wherein a multilayer flow that involves the interface of fluid is formed, are arranged on various positions of a substrate, and that each of the multilayer flow microchannels communicates with another multilayer flow microchannel.

Here, the substrate on which a plurality of multilayer flow microchannels are arranged may be a single substrate or a plurality of substrates laminated together. When a plurality of substrates are laminated with each other, one multilayer flow microchannel may be arranged on one substrate and as a whole, in other words, as an integrated structure, may constitute a substrate comprising a plurality of multilayer flow microchips.

The multilayer flow microchannels arranged on various positions may each be adapted to perform a single type of unit operation such as solvent extraction, or, alternatively, may each be adapted to perform different types of unit operations such as solvent extraction and a subsequent operation for chemical reaction. Further, each of the multilayer flow microchannels may be structured so as to enable the performance of a plurality of unit operations within a single multilayer flow microchannel. In either of the above-described multilayer flow microchannels, a parallel multilayer flow of two or more layers are formed.

The type of unit operation is not particularly restricted, and may be any physiochemical or chemical unit operation (including unit reactions) of various types. Needless to say, the unit operation includes operations for analysis or measurement.

In the invention of the present application, the multilayer flow inside the microchannel may form a liquid/liquid interface or a gas/liquid interface.

The most significant feature of the present invention lies in that three or more layers of parallel multilayer flow is formed, as described in the ninth, tenth and eleventh aspects of the invention.

Figure 1:
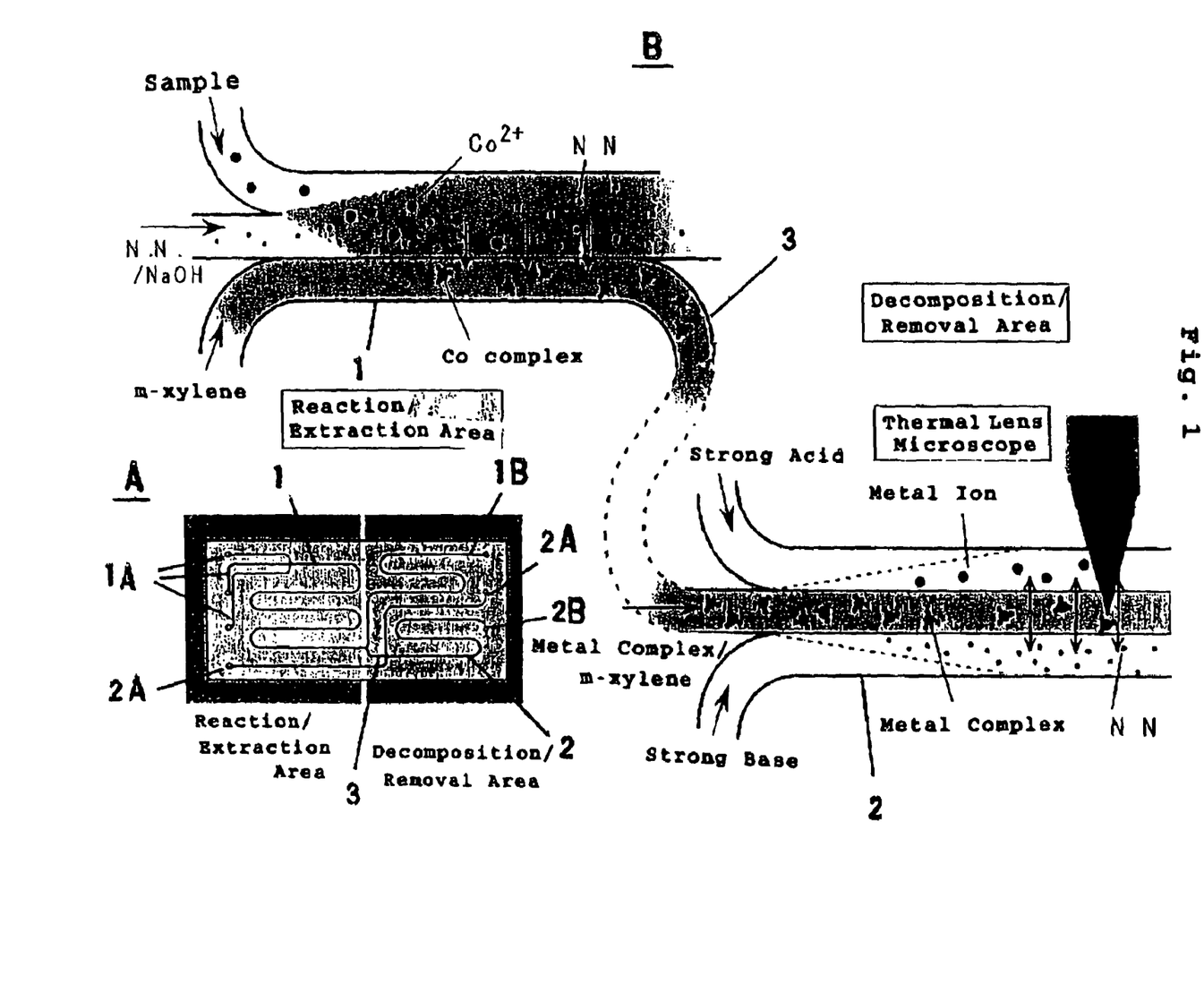
FIG. 1 is an illustration that exemplifies an overview of the present invention.
Figure 2:
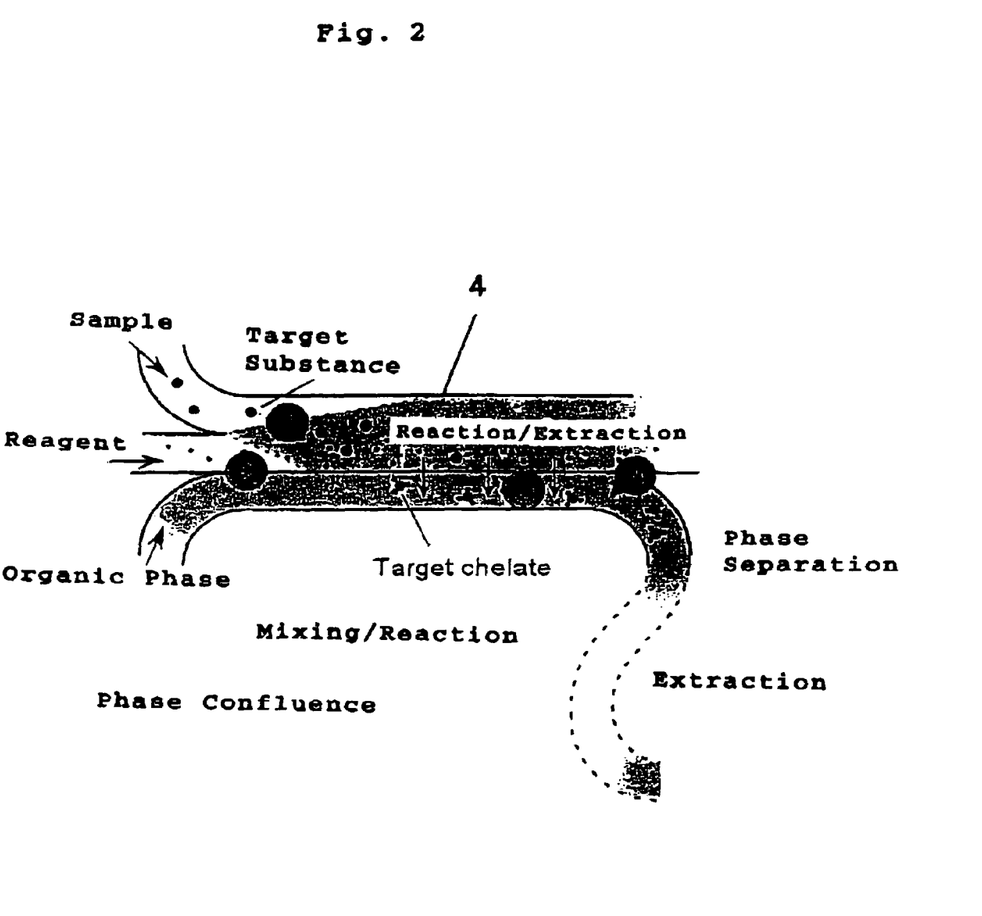
FIG. 2 is an illustration that exemplifies an overview of the present invention that is different from FIG. 1.

The present invention may be described, for example, by referring to the attached FIG. 1 and FIG. 2. First, as shown in FIG. 1(A), a first multilayer flow microchannel (1) that serves as a reaction/extraction area and a second multilayer flow microchannel (2) that serves as a decomposition/removal area may be arranged on two positions of the same substrate with the multilayer flow microchannels (1) and (2) being in communication with each other by way of a guide microchannel (3).

Further, at each of the multilayer flow microchannels (1) and (2), channel means (1A) and (2A) for supplying a liquid and channel means (1B) and (2B) for discharging a liquid are provided, respectively.

For example, in the structural example of FIG. 1(A), a system for selectively analyzing Co (Cobalt) in a sample containing Co ion and other metal ions may be constructed, as illustrated in FIG. 1(B). "N. N." in the Figure represents 2-nitroso-1-naphthol. In this example, $Co^{2+}$ in the sample is extracted to the m-xylene phase as a complex at the reaction/extraction area, and at the decomposition/removal area, metal ions other than $Co^{2+}$ are removed and only the content of $Co^{2+}$ is selectively detected by the thermal lens microscope.

In the reaction/extraction area of the first multilayer flow microchannel (1), a liquid/liquid interface of an aqueous/organic phase is formed and in the second multilayer flow microchannel (2), interfaces of three layers, i.e. hydrochloric acid-aqueous phase/m-xylene-organic phase/strong base-aqueous phase is formed.

As described above, the invention of the present application provides a system which enables the continuous performance of a plurality of operations at high efficiency, and is thus very useful for microanalysis, precise chemical synthesis and the like.

Further, as illustrated in FIG. 2, a plurality of unit operations may be carried out in a single multilayer flow microchannel (4). For example, as shown in FIG. 2, a plurality of unit operations such as: 1) mixing/reaction; 2) confluence of phases; 3) extraction; and 4) phase separation may be performed.

Figure 3:
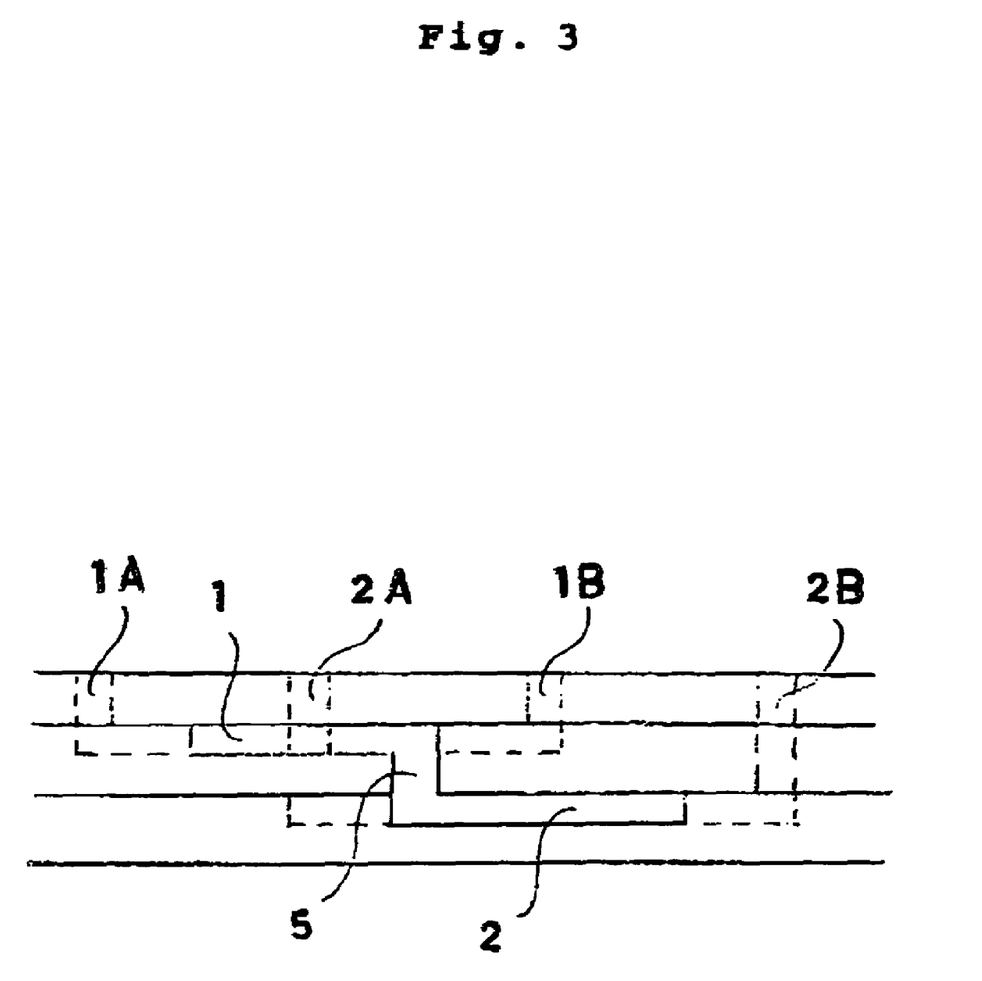
FIG. 3 is a schematic sectional view that exemplifies a three-dimensional configuration.

In the example of FIG. 1, a case in which the first multilayer flow microchannel (1) communicates with the second multilayer flow microchannel (2) by way of a guide microchannel (3) on the surface of the same substrate is described. However, the multilayer flow microchannels (1) and (2) do not necessarily have to be arranged on a surface of one substrate. For example, as in a chip structure wherein a plurality of substrates and intermediate plates are laminated to constitute a multilayer structure, such as that exemplified in FIG. 3 in which substrate (A), substrate (B) and cover plate (C) constitute a multilayer structure, the multilayer flow microchannels (1) and (2), the channel means for supplying a liquid (1A) and (2A), the channel means for discharging a liquid (1B) and (2B) may be configured in a three-dimensional manner. Further, the multilayer flow microchannels may communicate with another multilayer flow microchannel by way of a guide hole (5) that vertically penetrates through the substrates and intermediate plates, instead of a guide microchannel (3) arranged on the same substrate surface.

In the invention of the present application, one of the key features is the formation of a multilayer flow involving an interface within a microchannel. The microchannel itself may generally be formed by processing means of various types, including known means such as photolithography and wet etching. With regard to the substrate, substrates of various types, for example, those made of materials such as glass, silicon, resin and the like may be employed.

Regarding the dimensions of the microchannel, generally, the width thereof may be around 500 μm or less, and the depth thereof may be around 300 μm or less, and may be determined in accordance with the object and application of the multilayer flow microchannel structure.

Further, a microprojection may be formed at the bottom of the microchannel, at a position substantially corresponding to the positions of the parallel interfaces of the fluids forming the multilayer flow, and extending toward the flow direction. The microprojection is effective for forming a complete multilayer flow with stable interfaces and can be formed as ridges along the flow direction by an etching operation.

Furthermore, with regard to the multilayer flow involving interfaces of fluids, the above-mentioned dimensions of the microchannel, the flow rate within the microchannel and the flow amount can be established in accordance with the type and the composition of the target fluid. According to the knowledge obtained by the inventors of the present invention, the surface tension of the fluid primarily effects the formation of the multilayer flow involving the interface of fluids. Thus, the conditions for operating the microchannel multilayer flow system may be optimized taking into consideration such viewpoints.

Hereinafter, the aforementioned embodiment of the present invention will be described in further detail through the following Examples. It should be noted that the present invention is not restricted by these examples.

EXAMPLES

Example 1

A microchip with the multilayer flow microchannels having the channel pattern illustrated in FIG. 1(A) was produced.

Figure 4:
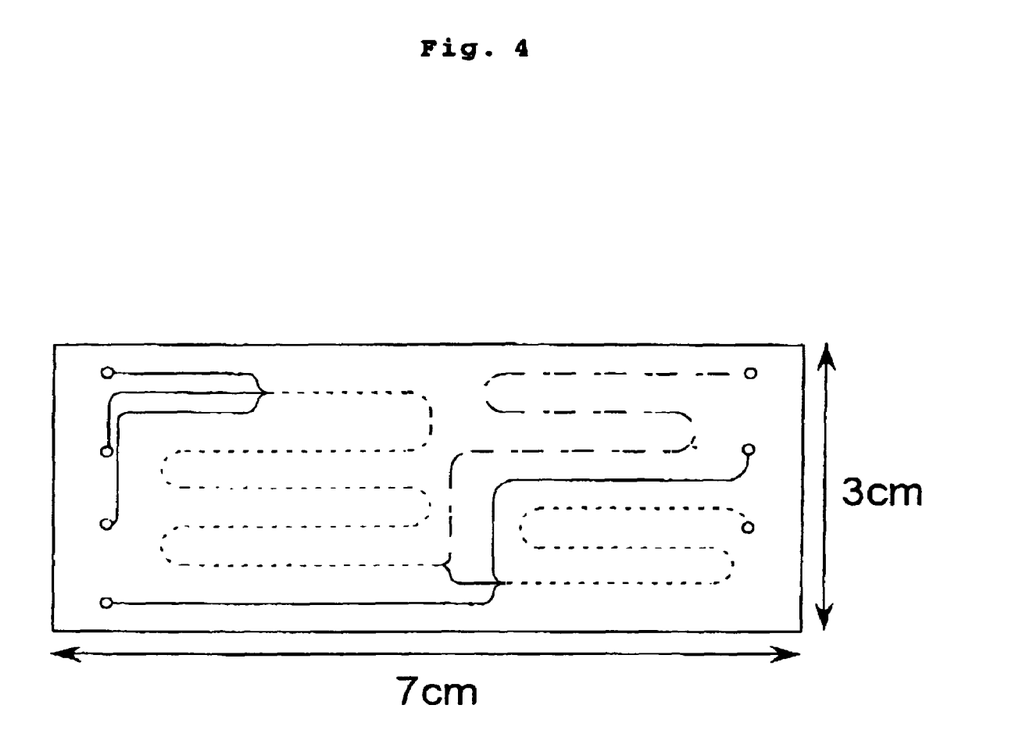
FIG. 4 is a planar view showing the structure of FIG. 1.

In the production of this microchip, microchannels were formed on a Pyrex glass substrate (3 cm×7 cm) by conventional photolithography and wet etching methods. In FIG. 4 showing the channel pattern of FIG. 1(A), the channels illustrated by solid lines were each formed as microchannels having a width of 50 μm and a depth of 20 μm. The channels illustrated by dotted lines were each formed as microchannels having a width of 140 μm and a depth of 20 μm. The channels illustrated by chained lines were each formed as microchannels having a width of 90 μm and a depth of 20 μm.

Figure 5:
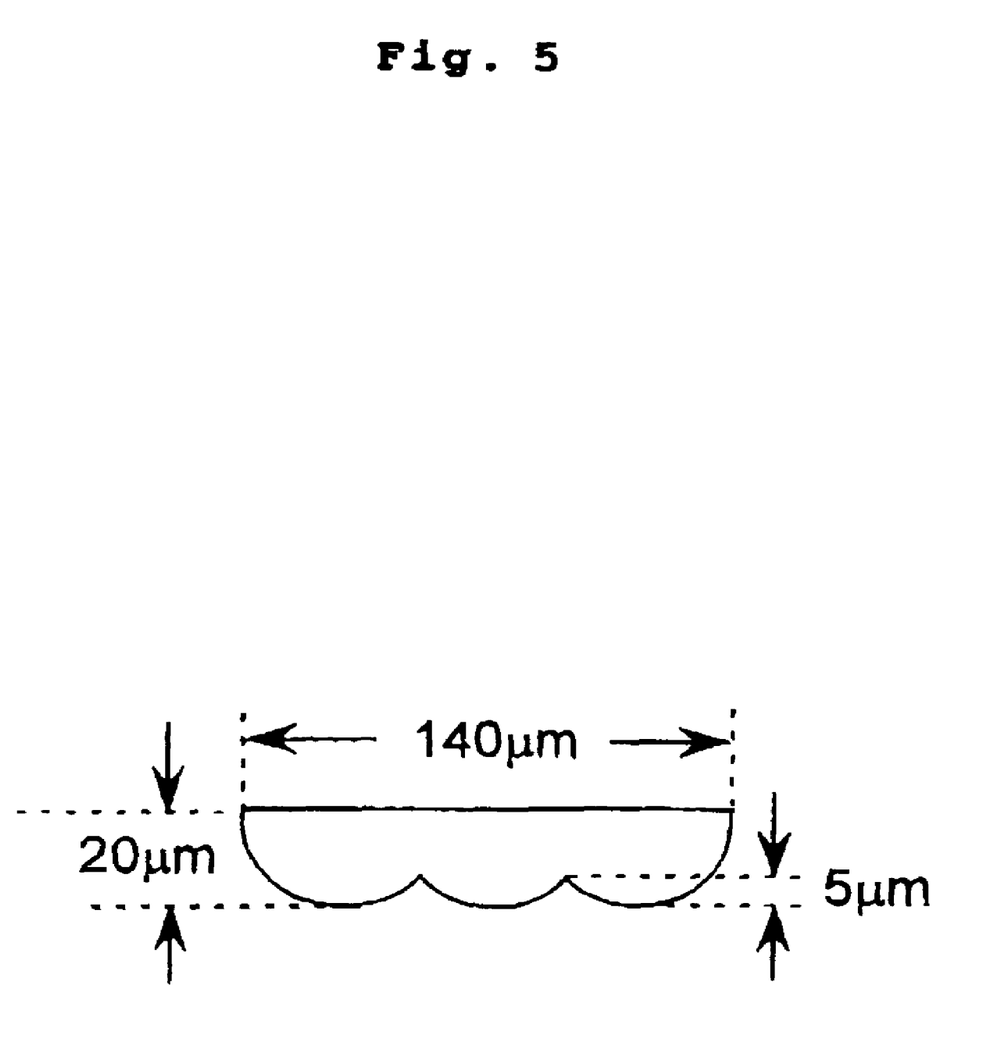
FIG. 5 is a sectional view that exemplifies the guide structure at the bottom of a microchannel.

Among the above-described microchannels, the microchannels illustrated by dotted lines each have a guide structure formed at their bottom. The guide structure is provided for stabilizing the interlayer portion of the multilayer flow, i.e., the liquid/liquid interface, and has a structure as shown in FIG. 5. Overall, at the bottom of the microchannel whose dimension is 140 μm width and 20 μm depth, two ridges having a height of 5 μm are arranged, and the presence of these two ridges cause the three-layer flow of liquid to be formed in a more stable manner.

The above-described structure, in which a liquid multilayer flow is stabilized by the projecting ridges formed at the bottom portion of the microchannel is a novel proposal by the present inventors and is very unique as well as significantly effective.

By using the thus produced microchip, Co(II) was selectively analyzed as shown in FIG. 1(A).

A sample aqueous solution containing Co(II) (containing $1 \times 10^{-6}$ M Cu(II) and 0.2 to $1.5 \times 10^{-7}$ M Co(II)), a $3.4 \times 10^{-4}$ M solution of 2-nitroso-1-naphthol (NN) containing NaOH, and m-xylene, were each introduced to the channel means for supplying liquid (1A) from separate supply inlets. Hydrochloric acid and an aqueous solution of NaOH were each introduced to the channel means for supplying liquid (2A).

In the reaction/extraction area, Co(II) in the sample was reacted and extracted to the m-xylene phase as a complex, and in the following decomposition/removal area, Cu(II), i.e., the metal ion other than Co(II), was removed. Thus, only the content of Co(II) in the m-xylene phase was detected by the thermal lens microscope.

Figure 6:
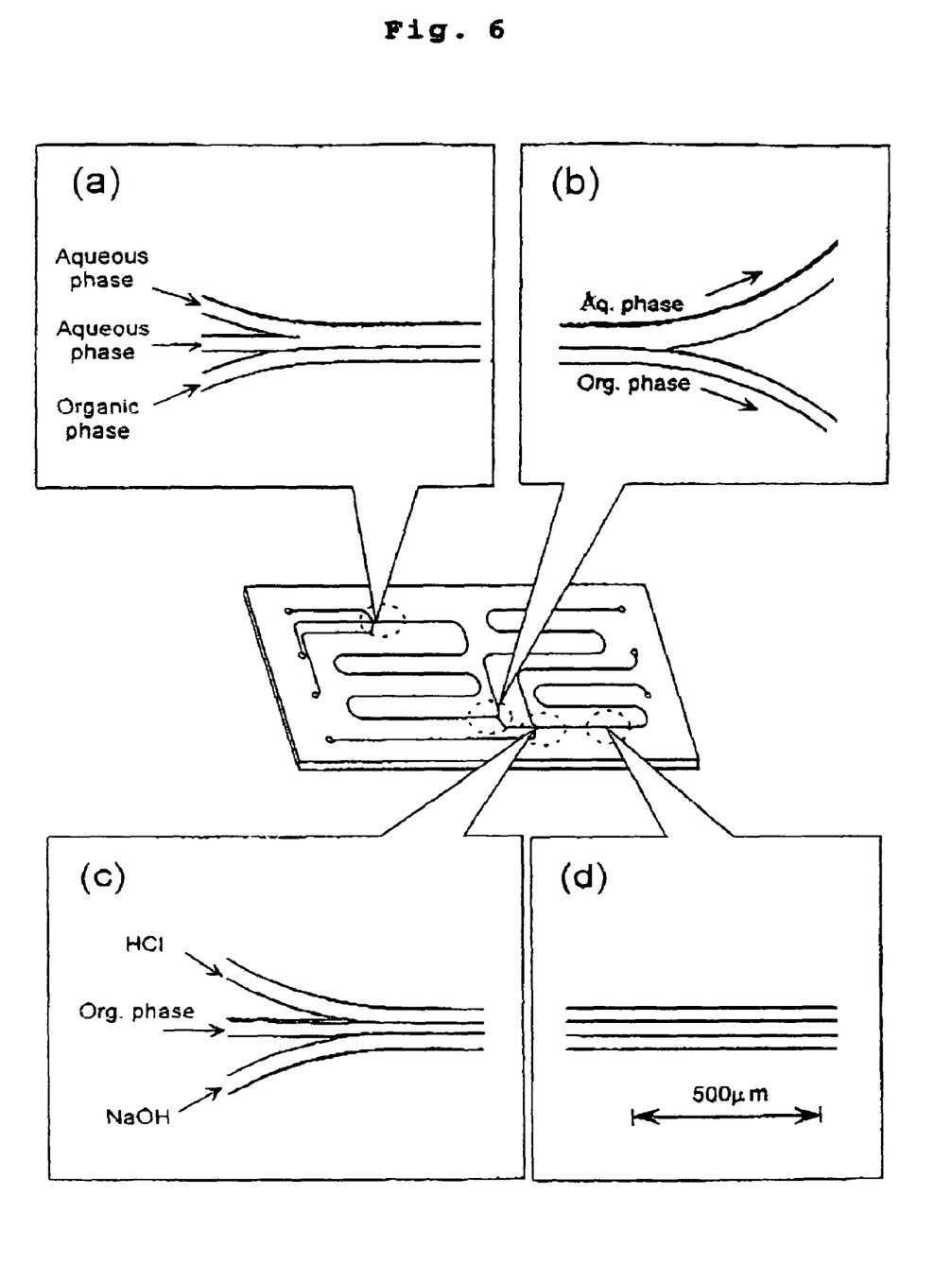
FIG. 6 is a view and photograph each showing the formation of a multilayer flow within a microchannel.

FIG. 6 illustrates a state of liquid/liquid multilayer flow formation, by photograph. The photographs show the status at the following sites:

(a) Junction point of aqueous phase and m-xylene phase
(b) Phase-separating point
(c) Junction point of HCL phase, m-xylene phase and NaOH aqueous phase
(d) Three-layer flow It was confirmed that a very stable multilayer flow was formed in the microchannel.

Figure 7:
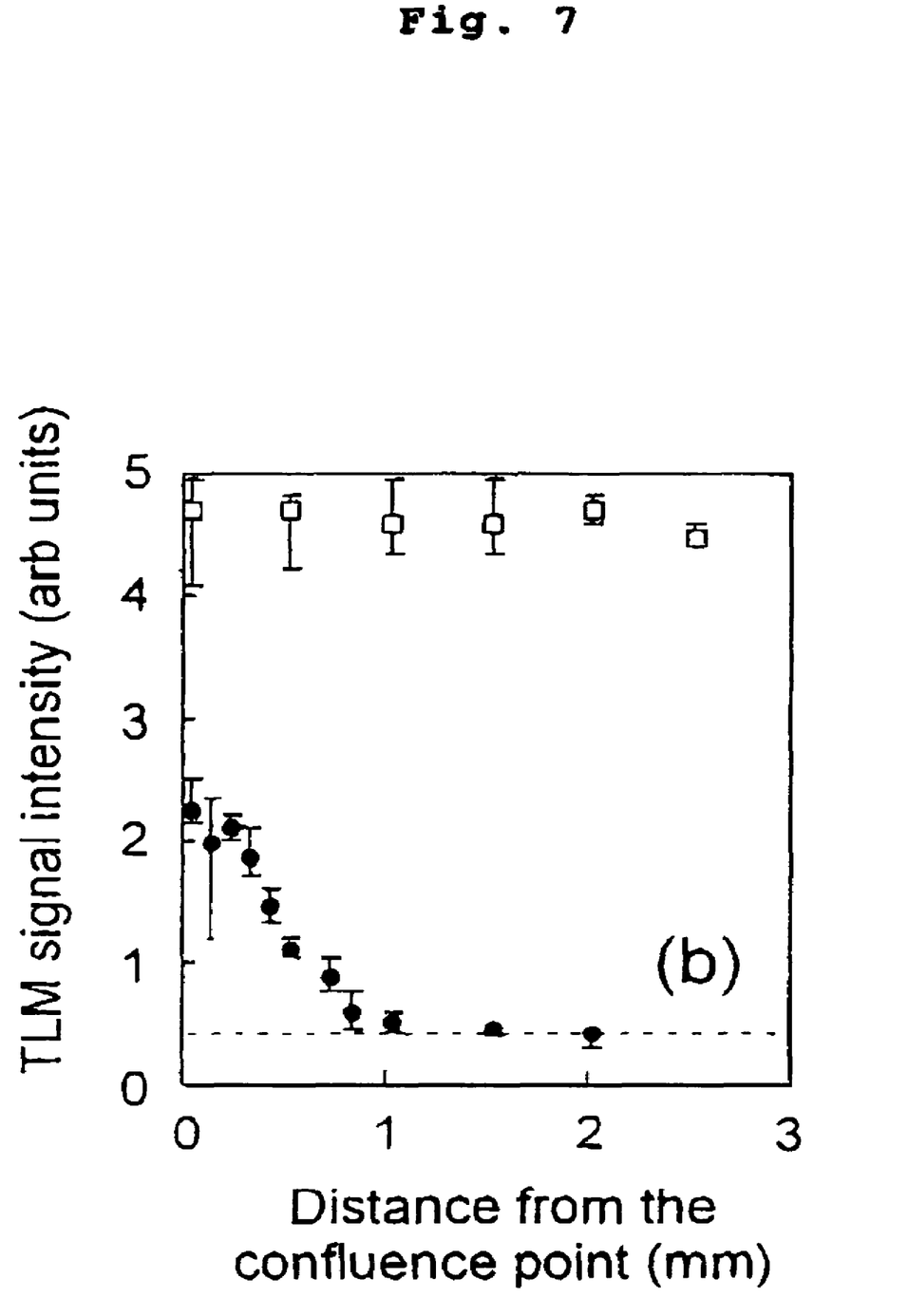
FIG. 7 is a graph showing the result of the detection of Co(II) using a thermal lens microscope in Example 1.

FIG. 7 shows the relationship between the distance from the junction point of FIG. 6(c) to the position at which measurement by thermal lens microscope was conducted, and the intensity of signals detected by the thermal lens microscope, for an aqueous sample containing Co(II) ($1 \times 10^{-7}$ M) and Cu(II) ($1 \times 10^{-6}$ M). The white square points in FIG. 7 represent signals of Co(II), and the black round points represent signals of Cu(II). From the measurement results obtained at a point approximately 1 mm from the junction point, it was determined that Co(II) was selectively detected.

Figure 8:
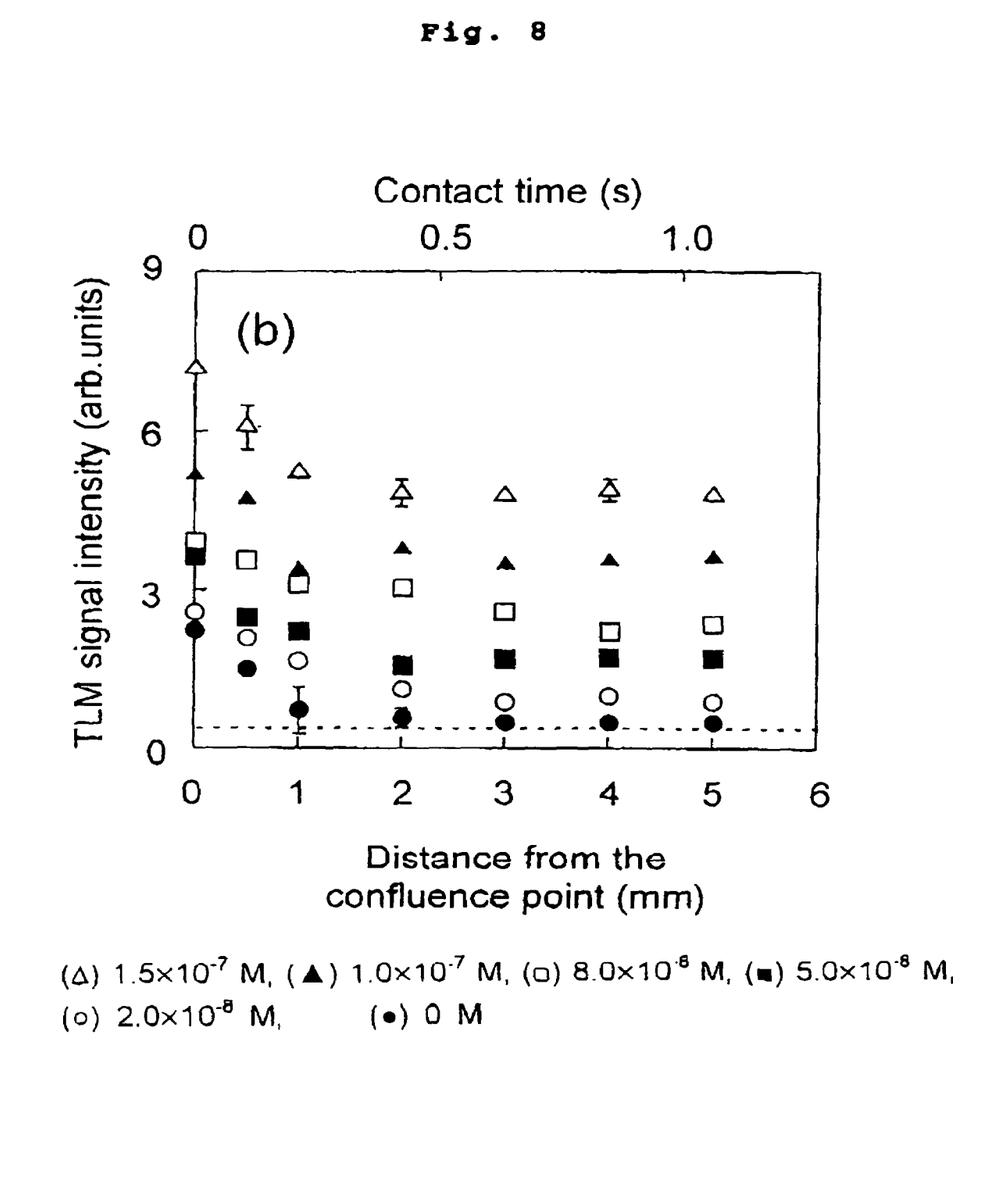
FIG. 8 is a graph showing the result of the detection of Co(II) of different concentrations.

Further, FIG. 8 shows the relationship between the distance from the aforementioned junction point (C) to the position at which measurement by thermal lens microscope was conducted, and the intensity of signals detected by the thermal lens microscope, in samples having different Co(II) concentrations (the concentration of Cu(II) was unchanged: $1 \times 10^{-6}$ M).

It can be seen that the Co(II) concentration was accurately reflected on the signal intensity.

Figure 9:
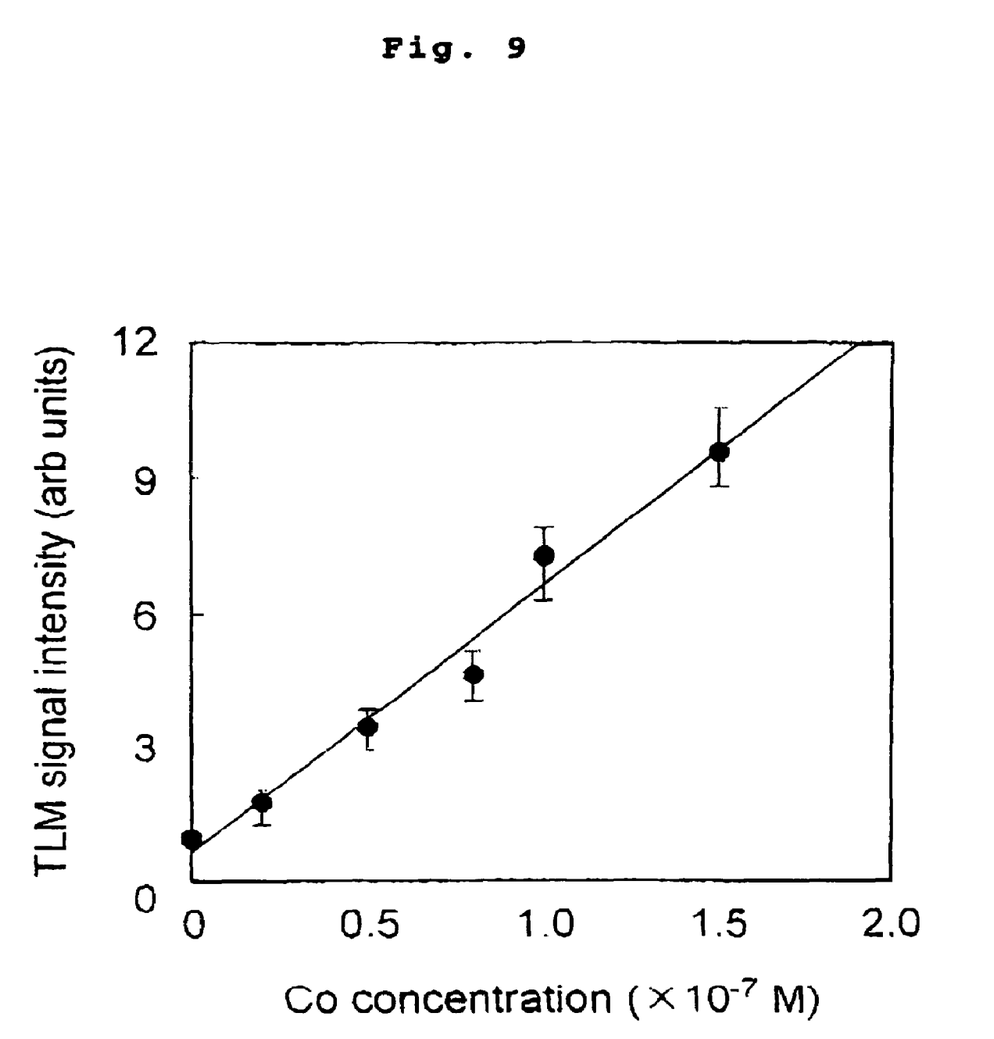
FIG. 9 is a graph showing the relationship between the concentration of Co(II) and the signal intensity detected by the thermal lens microscope.

FIG. 9 shows the relationship between the Co(II) concentration and the signal intensity of the thermal lens microscope obtained based on the aforementioned results, and exhibits excellent correlation.

Thus, all of the chemical operations necessary for Co analysis were successfully integrated and ultramicroanalysis of Co among coexisting metals was successfully achieved.

Further, it was confirmed that the multilayer flow microchannel system of the present invention is extremely effective.

Furthermore, it was confirmed that: when a guide structure consisting of a microprojection that substantially corresponds to the position of the interface is formed at the bottom of the multilayer flow microchannel, in the reaction/extraction area of the first half of the process, the aqueous/organic interface is formed in a stable manner, and in the second half of the process leading to the washing area, the aqueous solution and the extraction phase is completely separated. Thus, only the extraction phase is introduced to the washing area and by bringing an aqueous solution of hydrochloric acid and an aqueous solution of sodium hydroxide into contact with the extraction phase from the both sides thereof, a multilayer flow involving aqueous/organic/aqueous phase interfaces (a three-layer flow) is successfully formed in a more stable manner.

Example 2

Figure 10:
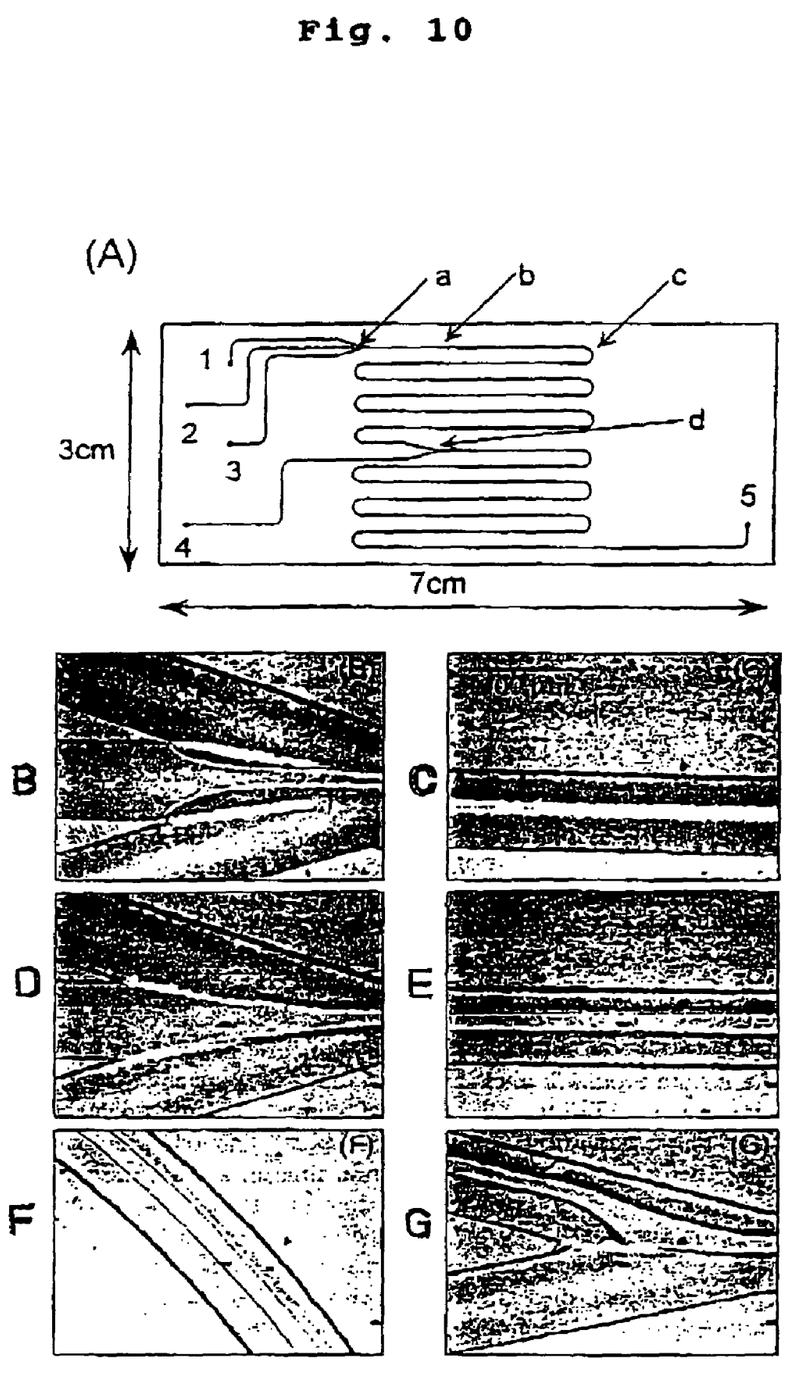
FIG. 10(A) is a planar view of the microchannel pattern used in Example 2 and FIGS. 10(B), 10(C), 10(D), 10(E), 10(F) and 10(G) are micrographs that illustrate the formation of multilayer flow.

The microchannel pattern shown in FIG. 10(A) was formed on a glass substrate by wet etching. The reference numbers 1, 2, 3 and 4 represent the fluid inlet parts and 5 represents the fluid discharge part. Further, symbols a and d in the figure each represent a fluid junction region, and a microchannel multilayer flow was formed between a and d, as well as on the downstream side of d. The distance between a and d was 18 cm. The width of the microchannel in which a multilayer flow was formed was 70 μm, and its depth was 30 μm.

The incident angle at which the flows join at the junction region point a was 18°. The incident angle at the junction region point d was 28°. The radius at point c was 1 mm.

In the above microchip consisting of microchannels formed on a substrate, from inlet 1: water (flow rate 5 μl/min);
from inlet 2: acetone (flow rate 3 μl/min); and from inlet 3: water (flow rate 5 μl/min)

were each introduced, and the flow rate between point a and point d was set at 13 cm/s. The Reynolds number was 10 or less and the fluids formed a multilayer flow.

FIG. 10(B) is a photograph showing the formation of a WAW (water/acetone/water) multilayer flow at the junction region of point a. FIG. 10(C) shows the WAW multilayer flow at point b which is located 10 mm downstream of point a.

Next, a microchannel multilayer flow was formed by using ethylacetate in place of acetone.

From inlet 1: water (flow rate 3 μl/min);
from inlet 2: ethylacetate (flow rate 5 μl/min);
from inlet 3: water (flow rate 3 μl/min); and
from inlet 4: water (flow rate 3 μl/min) was introduced and the flow rate between point a and point d was set at 11 cm/s. A WEW (water/ethylacetate/water) multilayer flow was formed and the thickness of the ethylacetate layer was determined to be 15 μm.

FIG. 10(D) shows the formation of WEW multilayer flow at the junction region of point a; FIG. 10(E) shows its state at point b; FIG. 10(F) shows its state at the curved point c; and FIG. 10(G) shows the state of WEW multilayer flow formation at the junction region point d.

Example 3

A multilayer flow microchannel with a width of 200 μm and a depth of 30 μm was formed on a glass substrate by wet etching. Using a microchip in which this microchannel was formed, the center m-xylene phase was sandwiched between two aqueous phases containing Co-dimethylaminophenol (CoDMAP) complex, as illustrated in FIG. 11(A), whereby a three-layer flow of aqueous phase/organic phase/aqueous phase was formed and extraction of CoDMAP to the m-xylene phase was effected.

The concentration of CoDMAP in the aqueous phases was set at $6.5 \times 10^{-6}$ M. Further, the flow rate of the aqueous phase was set at 0.5 μl/min, the flow rate of the organic phase was set at 1.0 μl/min, and the flow rate in the entire microchannel was 2.0 μl/min (0.56 cm/s).

The concentration of CoDMAP in the m-xylene organic phase was detected by using a thermal lens microscope system (TLM).

Figure 11:
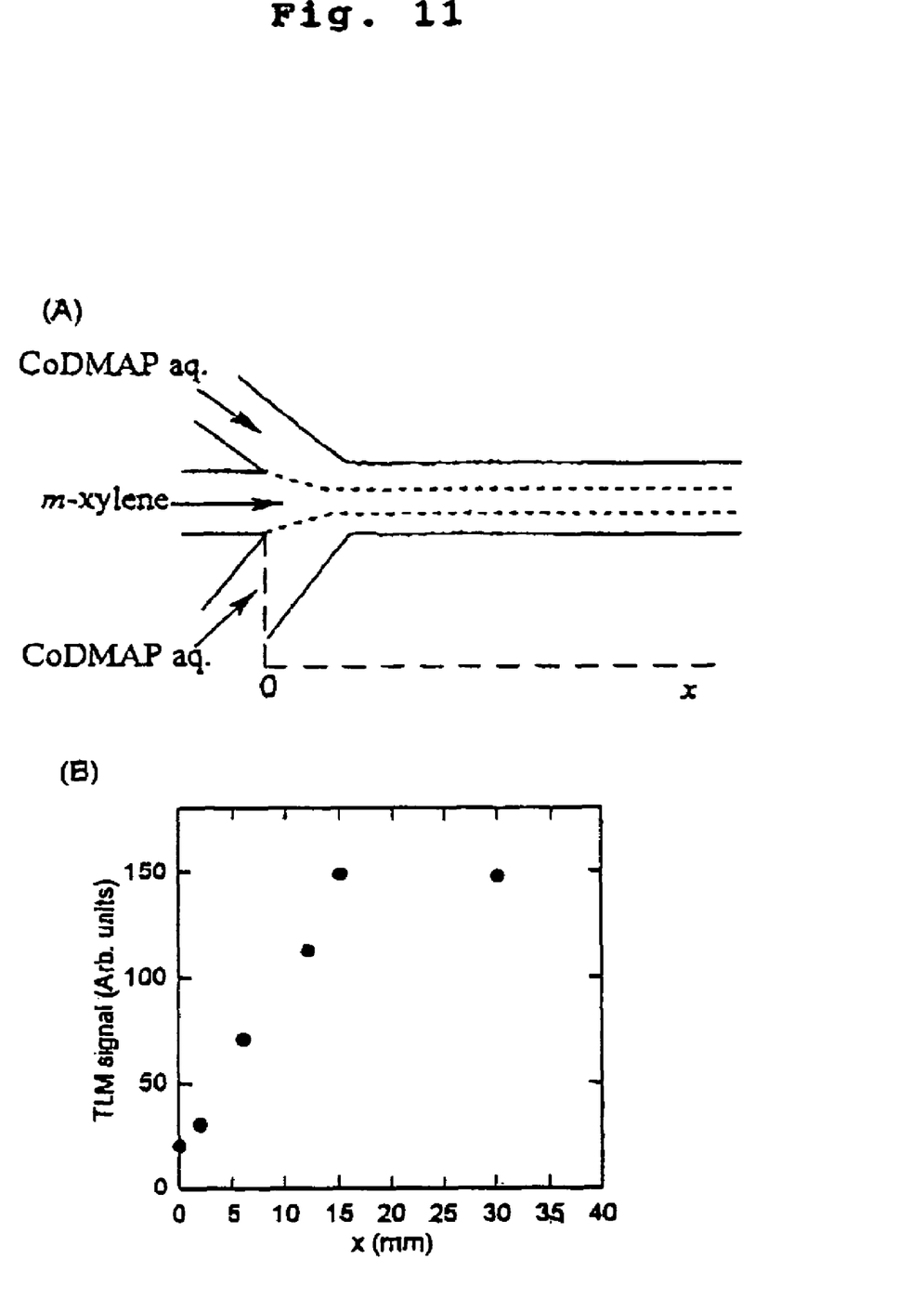
FIG. 11(A) is a schematic planar view of the microchannel of Example 3.
FIG. 11(B) is a graph showing the measurement result of the intensity of TLM detected.

FIG. 11(B) exemplifies the relationship between the distance X in FIG. 11(A) and the intensity of TLM signals.

It was confirmed that the extraction of CoDMAP had reached a state of equilibrium when the distance X was 1.5 cm, in other words, three seconds after the junction. These results suggest that this was an extraction operation of high efficiency.

Example 4

In a multilayer flow microchannel having a width of 200 μm and a depth of 30 μm, which was prepared in a manner similar to that described in example 3, a five-layer flow of butylacetate/water/butylacetate/water/butylacetate was formed and confirmed.

Figure 12:
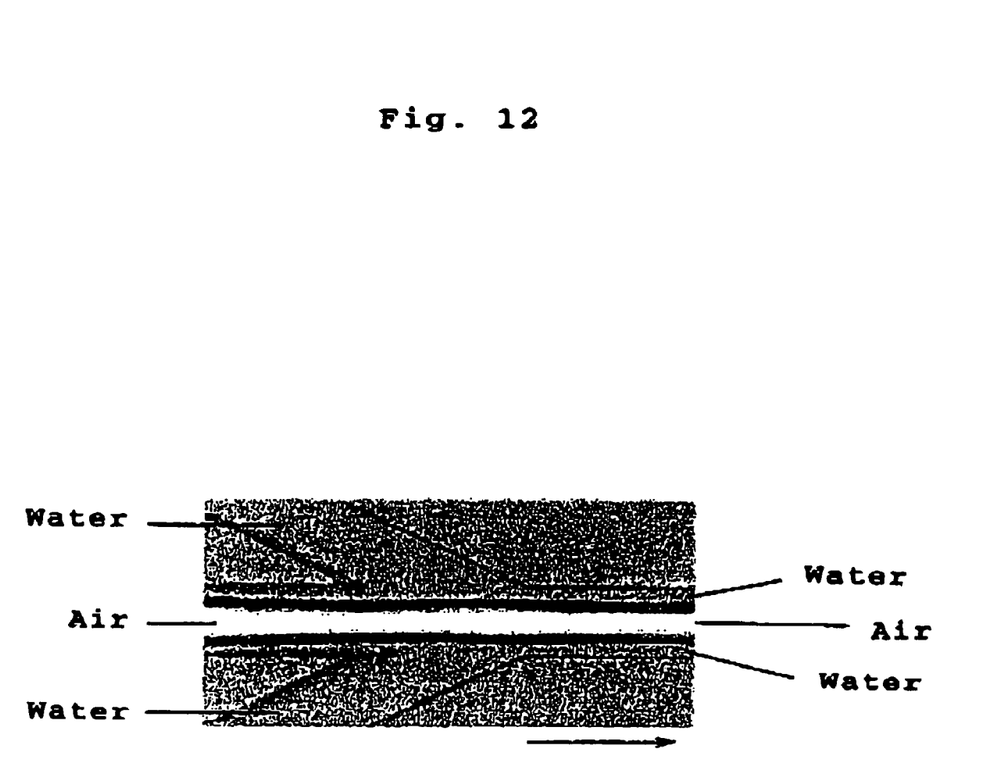
FIG. 12 is a micrograph illustrating the result obtained in Example 4.

Further, a three-layer flow having a gas/liquid interface of water/air/water was also formed and confirmed. FIG. 12 is a micrograph showing the state of such three-layer flow.

INDUSTRIAL APPLICABILITY

As described in detail above, the invention of the present application provides a highly integrated structure of multilayer flow microchannel, which enables the efficient performance of high-accuracy microanalysis, precise chemical synthesis or the like by continuous operation of a plurality of unit operations on a microchip, as well as a novel system for operating a multilayer flow.

The invention claimed is:

1. A method for multilayer flow operation to perform microanalysis or chemical synthesis,
the method utilizing a substrate having arranged thereon a first multilayer flow microchannel in which a parallel multilayer flow having at least one interface of fluids is formed, and a second multilayer flow microchannel in which a parallel multilayer flow having at least one interface of fluids is formed, the first multilayer flow microchannel and the second multilayer flow microchannel being in communication with each other, wherein a microprojection is formed at a bottom of at least one of the first multilayer flow microchannel and the second multilayer flow microchannel, the microprojection being formed at a position substantially corresponding to positions of parallel interfaces of the fluids forming the multilayer flow in at least one of the first multilayer flow microchannel and the second multilayer flow microchannel, and extending in a flow direction,
the method for multilayer flow operation comprising performing an extraction or a chemical reaction that involves a transfer of an analyte, a reactant or a product from one fluid layer within the first multilayer flow microchannel to another fluid layer within the first multilayer flow microchannel, and performing an extraction or a chemical reaction that involves a transfer of an analyte, a reactant or a product from one fluid layer within the second multilayer flow microchannel to another fluid layer within the second multilayer flow microchannel.

2. The method for multilayer flow operation of claim 1, wherein in at least one of the first multilayer flow microchannel and the second multilayer flow microchannel, a chemical reaction of reactants is performed in one fluid layer and an extraction of products from the one fluid layer to another fluid layer is performed.

3. The method for multilayer flow operation of claim 1, wherein the parallel multilayer flow in at least one of the first multilayer flow microchannel and the second multilayer flow microchannel includes three or more fluid layers, the parallel multilayer flow being used to perform an extraction or a chemical reaction that involves a transfer of an analyte, a reactant or a product from one fluid layer of the three or more fluid layers to another fluid layer of the three or more fluid layers.

4. The method for multilayer flow operation of claim 3, wherein an extraction or a chemical reaction that involves a transfer of an analyte, a reactant or a product from one fluid layer to another fluid layer is performed at each interface of the parallel multilayer flow that includes three or more fluid layers.

5. The method for multilayer flow operation of claim 4, wherein a chemical reaction that involves a transfer of a reactant or a product from one fluid layer to another fluid layer is performed at one interface of the parallel multilayer flow, and another chemical reaction that involves a transfer of a reactant or a product from one fluid layer to another fluid layer is performed at another interface of the parallel multilayer flow.

6. The method for multilayer flow operation of claim 4, wherein a chemical reaction that involves a transfer of a reactant or a product from one fluid layer to another fluid layer is performed at one interface of the parallel multilayer flow, and an extraction that involves a transfer of the product from one fluid layer to another fluid layer is performed at another interface of the parallel multilayer flow.

7. The method for multilayer flow operation of claim 1, wherein one fluid layer of the first multilayer flow microchannel is separated from the parallel multilayer flow of the first multilayer flow microchannel, and the one fluid layer joins the second multilayer flow microchannel.

* * * * *